US00PP17422P2

(12) United States Plant Patent
Westhoff

(10) Patent No.: US PP17,422 P2
(45) Date of Patent: Feb. 20, 2007

(54) ***GERANIUM* PLANT NAMED 'WESVILSU'**

(50) Latin Name: *Pelargonium peltatum*
Varietal Denomination: Wesvilsu

(75) Inventor: Heinrich Westhoff, Südlohn (DE)

(73) Assignee: J.+H. Westhoff Interpel, Südlohn (DE)

( * ) Notice: Subject to any disclaimer, the term of this patent is extended or adjusted under 35 U.S.C. 154(b) by 20 days.

(21) Appl. No.: 11/151,887

(22) Filed: Jun. 14, 2005

(51) Int. Cl.
*A01H 5/00* (2006.01)

(52) U.S. Cl. ..... Plt./332

(58) Field of Classification Search ..... Plt./332
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Ivy *Geranium* plant named 'Wesvilsu', characterized by its upright, outwardly spreading and trailing plant habit; vigorous growth habit; freely basal branching habit; large single red-colored flowers; and good garden performance.

2 Drawing Sheets

Botanical designation: *Pelargonium peltatum.*
Cultivar denomination: 'Wesvilsu'.

BACKGROUND OF THE INVENTION

The present invention relates to a new and distinct cultivar of Ivy *Geranium* plant, botanically known as *Pelargonium peltatum,* and hereinafter referred to by the name 'Wesvilsu'.

The new Ivy *Geranium* is a product of a planned breeding program conducted by the Inventor in Südlohn, Germany. The objective of the breeding program was to develop new Ivy *Geraniums* with large flowers with attractive coloration.

The new Ivy *Geranium* originated from a cross-pollination made by the Inventor in 2001 of a proprietary selection of *Pelargonium peltatum* identified as code number 01P06, not patented, as the female, or seed, parent with a proprietary selection of *Pelargonium peltatum* identified as code number 01P16, not patented, as the male, or pollen, parent. The cultivar Wesvilsu was discovered and selected by the Inventor as a flowering plant within the progeny from the stated cross-pollination in a controlled environment in Südlohn, Germany.

Asexual reproduction of the new cultivar by terminal cuttings in a controlled environment in Südlohn, Germany since 2002 shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Wesvilsu'. These characteristics in combination distinguish 'Wesvilsu' as a new cultivar and distinguish it from other known Ivy *Geranium* cultivars:

1. Upright, outwardly spreading and trailing plant habit.
2. Vigorous growth habit.
3. Freely basal branching habit.
4. Large single red-colored flowers.
5. Good garden performance.

Plants of the new Ivy *Geranium* differ from plants of the female parent selection in the following characteristics:

1. Plants of the new Ivy *Geranium* have shorter internodes than plants of the female parent selection.
2. Plants of the new Ivy *Geranium* have smaller leaves than plants of the female parent selection.
3. Plants of the new Ivy *Geranium* have more intense red-colored petals than plants of the female parent selection.

Plants of the new Ivy *Geranium* differ from plants of the male parent selection in the following characteristics:

1. Plants of the new Ivy *Geranium* have longer internodes than plants of the male parent selection.
2. Plants of the new Ivy *Geranium*
3. Plants of the new Ivy *Geranium* have larger flower umbels and larger flowers than plants of the male parent selection.
4. Plants of the new Ivy *Geranium* have lighter red-colored petals than plants of the male parent selection.

Plants of the new Ivy *Geranium* can be compared to plants of the cultivar Ville de Paris, not patented. In side-by-side comparisons conducted in Südlohn, Germany, plants of the new Ivy *Geranium* differed from plants of the cultivar Ville de Paris in the following characteristics:

1. Plants of the new Ivy *Geranium* were smaller and had shorter internodes than plants of the cultivar Ville de Paris.
2. Plants of the new Ivy*Geranium* had darker green-colored lateral branches than plants of the cultivar Ville de Paris.
3. Plants of the new Ivy*Geranium* had larger umbels and flowers than plants of the cultivar Ville de Paris.
4. Plants of the new Ivy *Geranium* had more intense red-colored petals than plants of the cultivar Ville de Paris.

Plants of the new Ivy*Geranium* can also be compared to plants of the cultivar Decora, not patented. In side-by-side comparisons conducted in Südlohn, Germany, plants of the new Ivy *Geranium* differed from plants of the cultivar Decora in the following characteristics:

1. Plants of the new Ivy *Geranium* were smaller and had shorter internodes than plants of the cultivar Decora.
2. Plants of the new Ivy *Geranium* had darker green-colored lateral branches than plants of the cultivar Decora.
3. Plants of the new Ivy *Geranium* had larger umbels and flowers than plants of the cultivar Decora.
4. Plants of the new Ivy *Geranium* had more intense red-colored petals than plants of the cultivar Decora.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photographs may differ slightly from the color values cited in the detailed botanical description which accurately describe the colors of the new Ivy*Geranium*.

The photograph on the first sheet comprises a side perspective view of typical flowering plants of 'Wesvilsu' grown in a window box container.

The photograph on the second sheet is a close-up view of a typical flower umbel of 'Wesvilsu'.

DETAILED BOTANICAL DESCRIPTION

Plants of the cultivar Wesvilsu have not been observed under all possible environmental conditions. The phenotype may vary somewhat with variations in environment, such as temperature and light intensity, without, however, any variance in genotype.

The aforementioned photographs, following observations and averaged measurements describe plants grown during the summer in containers in Südlohn, Germany, and under commercial practice in a glass-covered greenhouse with day temperatures ranging from 20 to 25° C., night temperatures ranging from 16 to 18° C. and light levels ranging from 3,000 to 50,000 lux. Plants used for the photographs were about four months old and plants used for the description were about eight months old. In the following description, color references are made to The Royal Horticultural Society Colour Chart, 2001 Edition, except where general terms of ordinary dictionary significance are used.

Botanical classification: *Pelargonium peltatum* cultivar Wesvilsu.

Parentage:

*Female, or seed, parent.*—Proprietary selection of *Pelargonium peltatum* identified as code number 01P06, not patented.

*Male, or pollen, parent.*—Proprietary selection of *Pelargonium peltatum* identified as code number 01P16, not patented.

Propagation:

*Type cutting.*—Terminal cuttings.

*Time to initiate roots.*—Summer: About 10 days at 20° C. Winter: About 14 days at 20° C.

*Time to produce a rooted young plant.*—Summer: About four weeks at 20° C. Winter: About five weeks at 20° C.

*Root description.*—Fine, fibrous; white in color.

*Rooting habit.*—Freely branching; dense.

Plant description:

*General appearance.*—Upright, outwardly spreading, trailing and eventually cascading plant habit; uniformly mounded; densely foliated.

*Growth and branching habit.*—Vigorous growth habit. Freely basal branching habit; lateral branches developing at potentially every node.

*Plant height, to top of umbels.*—About 22.7 cm.

*Plants height, to top of foliar plane.*—About 12 cm.

*Plant length.*—About 70 cm.

*Main branches.*—Length: About 60 cm. Diameter: About 4.3 mm. Internode length: About 5.5 cm. Texture: Pubescent. Color: 137B overlain with N199D.

*Lateral branches.*—Length: About 36.8 cm. Diameter: About 3.75 mm. Internode length: About 3.9 cm. Texture: Pubescent. Color: 137B.

*Foliage description.*—Arrangement: Opposite; simple. Length: About 4.1 cm. Width: About 6.4 cm. Shape: Palmately-lobed. Apex: Acute. Base: Cordate; open. Margin: Lobed; undulate. Venation pattern: Palmate. Texture, upper surface: Smooth, glabrous; leathery. Texture, lower surface: Slightly pubescent; leathery. Color: Developing and fully expanded foliage, upper surface: 147A; venation, 147A. Developing and fully expanded foliage, lower surface: 147B; venation, 146A. Zonation pattern: Not observed. Petiole: Length: About 3.1 cm. Diameter: About 1.3 mm. Texture, upper and lower surfaces: Densely pubescent. Color, upper and lower surfaces: 147A.

Flower description:

*Flower arrangement.*—Red-colored flowers; single rotate flowers arranged in roughly hemispherical umbels arising from apical leaf axils. Umbels displayed above the foliage on strong peduncles. Flowers face upright to outwardly; flowers mostly flat. Flowers not persistent. Flowers not fragrant.

*Quantity of flowers.*—About 18 to 21 flower buds and open flowers per umbel.

*Flowering season.*—Year-round under greenhouse conditions. In the garden in Südlohn, Germany, flowering is continuous from April until frost in the autumn.

*Flower longevity.*—Individual flowers last about eight to ten days on the plant; umbels last about three to four weeks on the plant.

*Umbel diameter.*—About 11.1 cm.

*Umbel height.*—About 5.8 cm.

*Flower diameter.*—About 4.4 cm.

*Flower depth (height).*—About 1.3 cm.

*Flower buds.*—Length: About 1.4 cm. Diameter: About 5 mm. Shape: Lanceolate. Color: Close to 146A to 146B.

*Petals.*—Quantity per flower: About five. Length: About 2.5 to 3.1 cm. Width: About 1.3 to 1.4 cm. Shape: Oblanceolate. Apex: Slightly emarginate. Base: Attenuate. Margin: Entire. Texture, upper and lower surfaces: Smooth, glabrous; velvety to satiny. Color: When opening and fully opened, upper surface: 45B; venation, 53A or N79B; color becoming closer to 53C with development. When opening and fully opened, lower surface: 44A to 44B; venation, 53A or N79B to N79C; color becoming closer to 78D with development.

*Sepals.*—Quantity per flower: About nine to ten in about two whorls. Length: About 1 cm. Width: About 3 mm. Shape: Lanceolate. Apex: Acute. Base: Attenuate. Margin: Entire. Texture, upper and lower surfaces: Smooth, glabrous. Color, upper and lower surfaces: 146A to 146B.

*Peduncle* (*umbel stem*).—Length: About 7 cm. Diameter: About 2 mm. Strength: Strong; wiry. Texture: Pubescent. Color: 146A.

*Pedicel* (*individual flower stem*).—Length: About 3.3 cm. Diameter: About 1.6 mm. Strength: Strong. Texture: Pubescent. Color: 146B overlain with 166A to 166B.

*Reproductive organs.*—Androecium: Stamen quantity per flower: About seven. Filament length: About 1 to 4 mm. Filament color: N155D. Anther length: About 3 mm. Anther width: About 1.5 mm. Anther shape: Ovate. Anther color: 45C. Pollen amount: Moderate to abundant. Pollen color: 32A. Gynoecium: Pistil quantity per flower: One. Pistil length: About 1.3 cm. Stigma diameter: About 4 mm. Stigma shape: Five-parted. Stigma color: 59A to 59C. Style length: About 5 mm. Style color: N155D. Ovary length: About 5 mm. Ovary diameter: About 2.5 mm. Ovary color: 136D.

*Seed.*—Seed development has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from 5 to 30° C. and have demonstrated good garden performance.

It is claimed:

1. A new and distinct cultivar of Ivy *Geranium* plant named 'Wesvilsu', as herein illustrated and described.

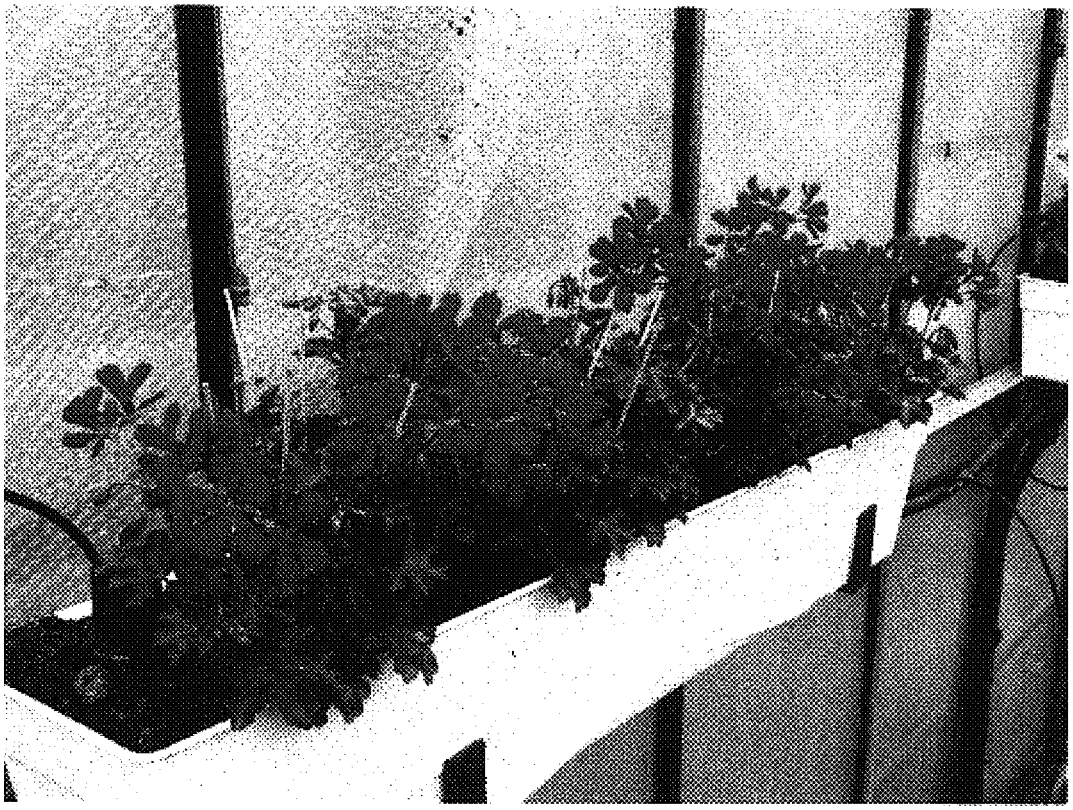

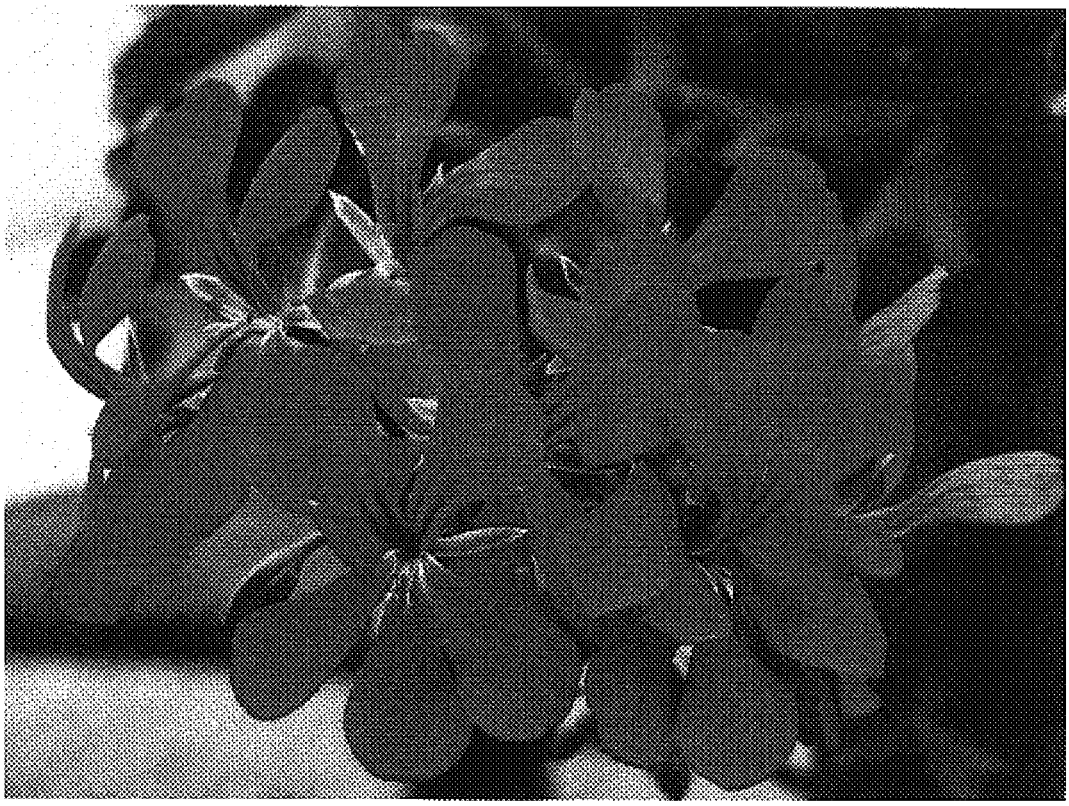

* * * * *